US 9,907,698 B2

(12) United States Patent
Cooper et al.

(10) Patent No.: US 9,907,698 B2
(45) Date of Patent: Mar. 6, 2018

(54) APPARATUS FOR PHOTOTHERAPY OF THE EYE

(71) Applicant: TECLens, LLC, St. James, NY (US)

(72) Inventors: Frank George Cooper, Dix Hills, NY (US); Patrick David Lopath, Stamford, CT (US); David E. Acker, St. James, NY (US); David L. Gershaw, Charlestown, MA (US)

(73) Assignee: TECLens, LLC, St. James, NY (US)

( * ) Notice: Subject to any disclaimer, the term of this patent is extended or adjusted under 35 U.S.C. 154(b) by 693 days.

(21) Appl. No.: 14/314,518

(22) Filed: Jun. 25, 2014

(65) Prior Publication Data
US 2014/0379054 A1   Dec. 25, 2014

Related U.S. Application Data

(60) Provisional application No. 61/839,016, filed on Jun. 25, 2013.

(51) Int. Cl.
*A61N 5/06* (2006.01)
*A61B 18/20* (2006.01)
(Continued)

(52) U.S. Cl.
CPC ............ *A61F 9/0079* (2013.01); *A61F 9/009* (2013.01); *A61F 2009/00872* (2013.01);
(Continued)

(58) Field of Classification Search
None
See application file for complete search history.

(56) References Cited

U.S. PATENT DOCUMENTS

| 3,589,800 A | * | 6/1971 | Cardona | ............... A61B 3/117 351/159.02 |
| 3,641,332 A | * | 2/1972 | Reick | ..................... A61B 1/07 264/1.24 |

(Continued)

FOREIGN PATENT DOCUMENTS

| DE | 102010016629 A1 | 10/2011 |
| EP | 1561440 A1 | 8/2005 |

(Continued)

OTHER PUBLICATIONS

Partial International Search Report for Application No. PCT/US2014/044091 dated Nov. 4, 2014.

(Continued)

*Primary Examiner* — Lynsey Eiseman
*Assistant Examiner* — Manolis Pahakis
(74) *Attorney, Agent, or Firm* — Lerner, David, Littenberg, Krumholz & Mentlik, LLP

(57) ABSTRACT

A device and method for applying light to the cornea of the eye as, for example, to promote crosslinking of collagen in the cornea for vision correction. The device may include a structure having form and size similar to a conventional contact lens. The structure may include an optically dispersive element such as a mass of an optically dispersive material that may be contained in a cavity of a reflective element. Light applied to the dispersive mass as, for example, by an optical fiber connected to the structure is dispersed in the structure and passes into the cornea. The patient may blink or close the eye during the procedure, which increases patient comfort and aids in maintaining hydration of the cornea.

16 Claims, 9 Drawing Sheets

(51) Int. Cl.
    *G02C 7/04*     (2006.01)
    *A61F 9/00*     (2006.01)
    *A61F 9/01*     (2006.01)
    *A61F 9/007*    (2006.01)
    *A61F 9/009*    (2006.01)
    *A61F 9/008*    (2006.01)

(52) U.S. Cl.
    CPC    *A61N 2005/063* (2013.01); *A61N 2005/0648* (2013.01); *A61N 2005/0651* (2013.01); *A61N 2005/0661* (2013.01); *G02C 7/04* (2013.01)

(56) References Cited

U.S. PATENT DOCUMENTS

| | | | | |
|---|---|---|---|---|
| 3,944,341 | A * | 3/1976 | Pomerantzeff | A61B 3/0008 351/206 |
| 4,014,321 | A * | 3/1977 | March | A61B 5/14558 356/39 |
| 4,265,519 | A * | 5/1981 | Pomerantzeff | A61B 3/0008 351/205 |
| 4,485,820 | A * | 12/1984 | Flower | A61B 5/14555 351/219 |
| 4,799,784 | A * | 1/1989 | Safir | A61B 3/10 351/212 |
| 4,871,247 | A * | 10/1989 | Haynes | G02B 6/06 351/205 |
| 4,932,954 | A * | 6/1990 | Wondrazek | A61B 17/22004 606/15 |
| 5,354,331 | A * | 10/1994 | Schachar | A61F 2/147 424/427 |
| 5,437,660 | A * | 8/1995 | Johnson | A61B 18/24 606/15 |
| 5,519,534 | A * | 5/1996 | Smith | A61N 5/062 250/228 |
| 5,521,657 | A * | 5/1996 | Klopotek | A61B 5/0095 351/212 |
| 5,582,608 | A * | 12/1996 | Brown | A61B 17/0231 606/4 |
| 5,618,284 | A | 4/1997 | Sand | |
| 5,688,264 | A * | 11/1997 | Ren | A61F 9/00821 606/13 |
| 5,824,023 | A * | 10/1998 | Anderson | A61B 18/203 607/88 |
| 5,830,139 | A * | 11/1998 | Abreu | A61B 5/14532 600/399 |
| 6,221,028 | B1 | 4/2001 | Lieberman et al. | |
| 6,267,752 | B1 * | 7/2001 | Svetliza | A61B 3/0008 600/205 |
| 7,077,544 | B2 * | 7/2006 | Parker | A61M 21/02 362/231 |
| 7,137,952 | B2 * | 11/2006 | Leonardi | G02C 7/04 600/398 |
| 7,241,291 | B2 * | 7/2007 | Kreindel | A61B 18/203 606/3 |
| 7,626,562 | B2 * | 12/2009 | Iwasaki | G02B 27/00 345/7 |
| 8,096,654 | B2 * | 1/2012 | Amirparviz | B29D 11/00826 345/8 |
| 8,556,425 | B2 * | 10/2013 | Frey | A61F 9/00825 351/208 |
| 9,389,433 | B2 * | 7/2016 | Pugh | G02C 7/04 |
| 2002/0141174 | A1 * | 10/2002 | Parker | A61M 21/02 362/612 |
| 2004/0196431 | A1 * | 10/2004 | Farberov | A61B 3/117 351/205 |
| 2005/0279354 | A1 * | 12/2005 | Deutsch | A61B 1/07 128/200.24 |
| 2007/0239232 | A1 * | 10/2007 | Kurtz | A61N 5/0613 607/87 |
| 2008/0208177 | A1 | 8/2008 | Mrochen et al. | |
| 2008/0287930 | A1 * | 11/2008 | Rapoport | A61B 18/203 606/9 |
| 2009/0149842 | A1 | 6/2009 | Muller et al. | |
| 2009/0161827 | A1 * | 6/2009 | Gertner | A61F 9/008 378/65 |
| 2009/0189974 | A1 | 7/2009 | Deering | |
| 2009/0198173 | A1 * | 8/2009 | Samuel | A61N 5/062 604/20 |
| 2010/0001926 | A1 | 1/2010 | Amirparviz et al. | |
| 2010/0016729 | A1 | 1/2010 | Futrell | |
| 2010/0082018 | A1 | 4/2010 | Panthakey et al. | |
| 2010/0094197 | A1 | 4/2010 | Marshall et al. | |
| 2010/0265461 | A1 * | 10/2010 | Gille | A61B 3/117 351/219 |
| 2010/0318017 | A1 | 12/2010 | Lewis et al. | |
| 2011/0001926 | A1 | 1/2011 | Mann et al. | |
| 2011/0190749 | A1 * | 8/2011 | McMillan | A61B 18/22 606/16 |
| 2011/0264082 | A1 | 10/2011 | Mrochen et al. | |
| 2011/0282333 | A1 | 11/2011 | Herekar et al. | |
| 2012/0199995 | A1 | 8/2012 | Pugh et al. | |
| 2012/0203161 | A1 | 8/2012 | Herekar | |
| 2012/0215291 | A1 * | 8/2012 | Pugh | A61M 21/02 607/93 |
| 2012/0257167 | A1 * | 10/2012 | Gille | A61B 3/117 351/219 |
| 2012/0310083 | A1 | 12/2012 | Friedman et al. | |
| 2013/0110091 | A1 | 5/2013 | Berry | |
| 2013/0211389 | A1 | 8/2013 | Chuck et al. | |
| 2013/0278887 | A1 * | 10/2013 | Legerton | G02C 11/00 351/158 |
| 2015/0265850 | A1 * | 9/2015 | Finger | A61N 5/1017 600/7 |

FOREIGN PATENT DOCUMENTS

| | | |
|---|---|---|
| EP | 2227197 A1 | 9/2010 |
| EP | 2380535 A1 | 10/2011 |
| EP | 2407132 A1 | 1/2012 |
| WO | 2007082127 A2 | 7/2007 |
| WO | 2011094758 A2 | 8/2011 |
| WO | 2012127330 A1 | 9/2012 |
| WO | 2012145853 A2 | 11/2012 |

OTHER PUBLICATIONS

International Search Report and Written Opinion for Application No. PCT/US2014/044091 dated Feb. 13, 2015.
"KXL II . . . The Future of Cross-Linking," Avedro, Inc. (2012).
Park, Sunju and Roy S. Chuck, "Corneal collagen cross-linking for correction of low myopia?" Copyright Lippincott Williams & Wilkins, Walters Kluwer Health (2013) www.co-ophthalmology.com.

* cited by examiner

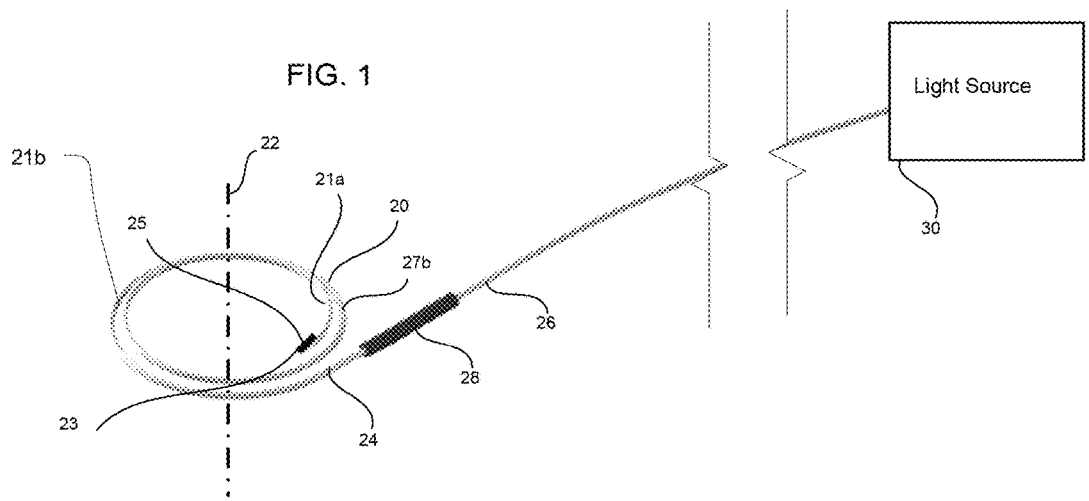
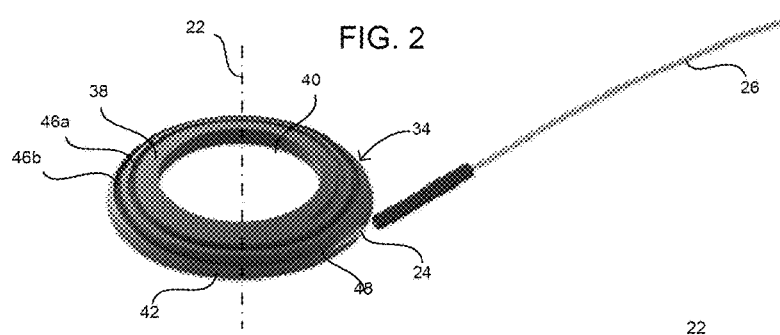
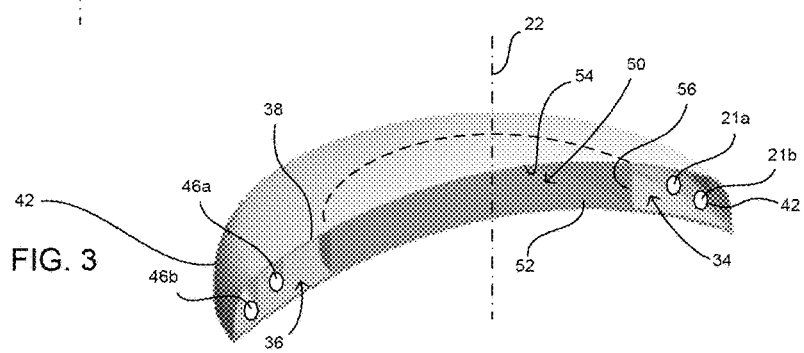

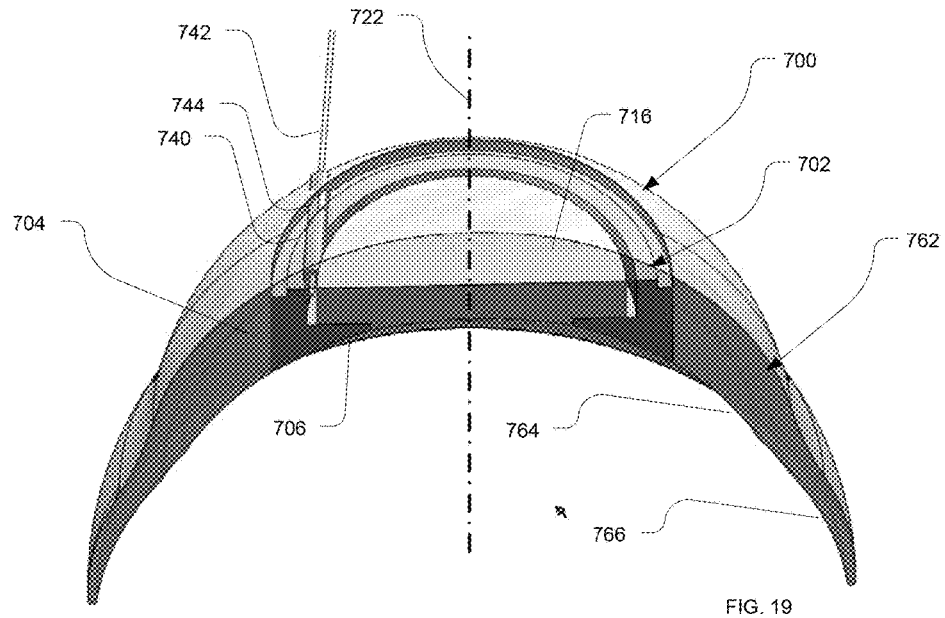
FIG. 19
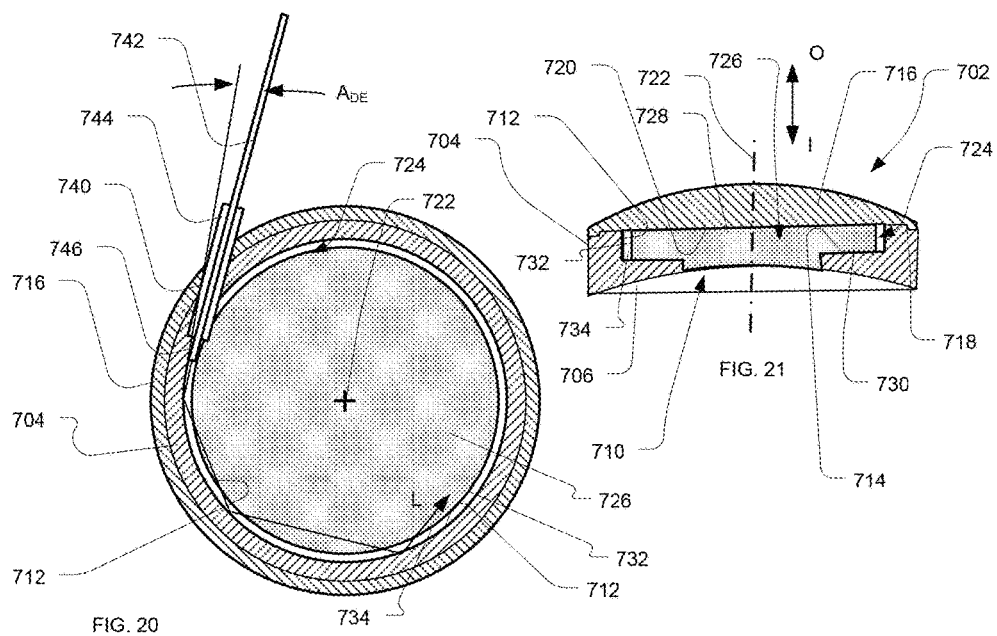
FIG. 20
FIG. 21

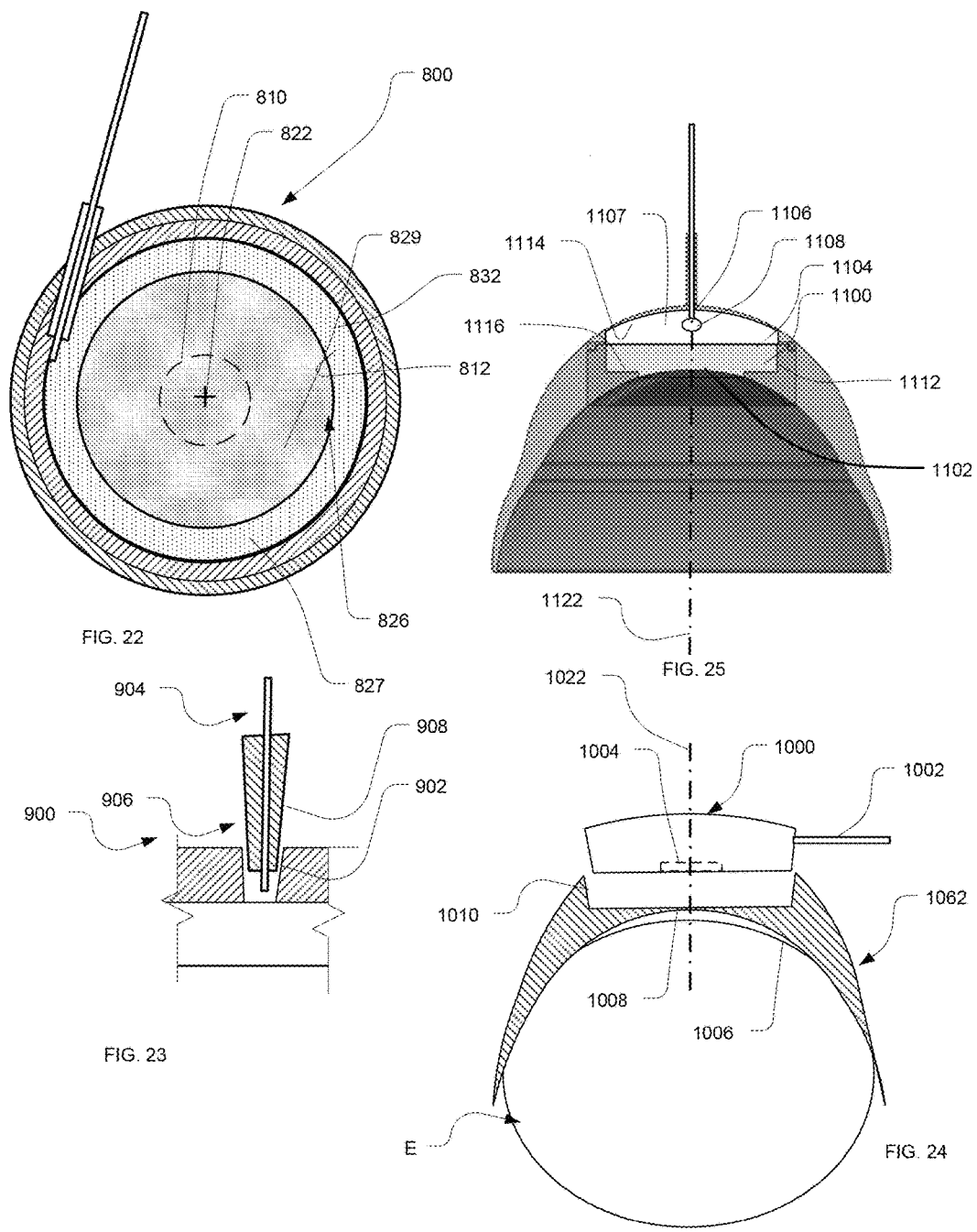

APPARATUS FOR PHOTOTHERAPY OF THE EYE

CROSS-REFERENCE TO RELATED APPLICATIONS

The present application claims the benefit of the filing date of U.S. Provisional Patent Application No. 61/839,016 filed Jun. 25, 2013, the disclosure of which is hereby incorporated herein by reference.

BACKGROUND OF THE INVENTION

The present application relates generally to devices for applying light such as ultraviolet ("UV") light to the cornea of the eye; to methods of manufacturing such devices; and to methods of applying phototherapy to the eye.

In humans and other mammals, the eye includes a clear, dome-shaped element referred to as the cornea disposed at the front of the eye. Light passes into the eye through the cornea and, after passing through other structures such as the iris and the lens of the eye, ultimately impinging on the retina. The light impinging on the retina is converted to neural impulses that are processed to form the visual images. The cornea and the lens refract the light passing through them. In a healthy eye, the refraction imparted by the cornea and the lens focuses the light on the retina.

Most of the light refraction required for the primary focusing on the retina is done by the cornea, with the lens making the accommodative changes to move focus from close to distant objects. Mismatches between the corneal curvature and the axial length of the eye, imperfections in the shape of the cornea, malpositions of the lens, and error in the vitreous of the eye can all lead to vision errors. For example, an eye that has a cornea that focuses the light in front of the retina (an eye with too much curvature relative to the axial length of the eye) suffers from myopia (also referred to as near-sightedness). Conversely, a cornea that is not curved enough for the axial length results in hyperopia (also referred to as far-sightedness), where the focal point is behind the retina. Astigmatism is an uneven curvature of the cornea with respect to the shape of the retina. All three conditions result in an out of focus image formed on the retina. Beyond these errors in curvature that affect healthy eyes, pathological conditions such as keratoconus and corneal ectasia result in unstable corneas and impaired vision.

Eyeglasses and contact lenses can correct conditions such as myopia, hyperopia and astigmatism by adding an artificial refractive element to the system. However, these devices impose some inconvenience on the patient. Accordingly, refractive surgical therapies such as radial keratotomy and laser ablation of the cornea have been developed. These procedures correct vision by reshaping the cornea so as to alter its refractive properties. However, these procedures have certain drawbacks and can have undesirable side effects.

In a technique known as orthokeratolgy, the cornea is mechanically reshaped by applying a rigid contact lens having a shape different from the existing shape of the cornea. The lenses are worn overnight. However, changes in shape induced by orthokeratology are temporary. They typically last only 24-48 hours, after which the cornea reverts to its original shape.

In yet another technique, the cornea can be reshaped by crosslinking fibers of collagen which form part of the cornea. The crosslinking can be performed by applying UV light to the cornea in conjunction with a chemical agent such as riboflavin. Typically, the UV light is applied by directing UV light from one or more light emitting diodes ("LEDs") m into the patient's eye, substantially perpendicular to the surface of the cornea. The crosslinking strengthens the cornea and can also cause reshaping of the cornea Procedures of this type require that the patient keep the treated eye open for a prolonged period without blinking. This creates discomfort for the patient and also requires close monitoring by trained personnel to assure that the cornea remains hydrated.

It has also been proposed to apply crosslinking in conjunction with orthokeratology. In this approach, the crosslinking is performed after mechanical reshaping or while the cornea is held mechanically in the desired shape. The crosslinking acts to set the cornea and prevent reversion of the cornea to its original shape. For example, Mrochen et al., U.S. Published Patent Application No. 2008/0208177, proposes a thick, rigid mold equipped with an array of light emitting diodes or "LED's." While the mold is applied to the cornea, the LED's emit UV light in the direction toward the surface of the cornea. The mold may include a diffuser plate interposed between the LED's and the cornea to make the light impinging on the cornea more uniform. In another variant, the array of LED's and the diffuser plate is replaced by a branching array of "optical light guides" extending to numerous points on the surface of the cornea. Structures of this type still require that the patient keep his or her eye open during the treatment, without blinking.

Chuck et al., U.S. Published Patent Application No. 2013/0211389, discloses a treatment device which incorporates radiation-emitting elements such as LEDs, along with the circuitry required to drive these elements, into a device having size and shape resembling a conventional contact lens. Using this device, the patient can blink or keep his or her eye shut while receiving crosslinking therapy. This provides a more comfortable patient experience, greatly reduces the risk of corneal dehydration during the therapy, and also reduces the need for constant monitoring of hydration by medical personnel. However, LEDs and circuitry incorporated into the device evolve heat during operation. Therefore, the power which can be applied by the device must be restricted.

BRIEF SUMMARY OF THE INVENTION

One aspect of the present invention provides a device for applying light to the eye of a human or other mammalian subject. A device according to this aspect of the present invention desirably includes a contact lens structure having a first inner surface generally corresponding to the shape of the cornea. Optionally, the device may have a second interior surface corresponding to the shape of the sclera. The contact lens structure desirably includes an optically dispersive element. The optically dispersive element desirably is constructed and arranged so that light passing into the optically dispersive element in a direction generally parallel to the inner surface will be dispersed and at least some of the dispersed light will pass through the inner surface of the contact lens structure into the cornea.

The optically dispersive element may include an optically dispersive fiber. The optically dispersive fiber may be arranged in one or more loops encircling a central axis of the contact lens structure. Alternatively or additionally, the optically dispersive element may include an optically dispersive mass, and the mass may have an inner surface having a shape generally conforming to the shape of the cornea. In certain embodiments, the structure includes both an optically dispersive fiber and an optically dispersive mass. The optically dispersive fiber may be in optical communication with the optically dispersive mass, so that light dispersed by the fiber will pass into the mass, and will be further dispersed by the mass and pass into the cornea. Desirably, the structure includes a reflector that defines a cavity encompassing the dispersive mass. In one arrangement, a transmission optical fiber has a distal end disposed within the cavity, and the light is dispersed by the dispersive mass and passes out through an aperture in the reflector.

The entire contact lens structure may be formed as a shell generally conforming to the shape of the eye. The thickness of the shell may be similar to that of a conventional contact lens as, for example, less than about 1 mm thick.

A further aspect of the present invention provides methods of applying phototherapy to the eye of human or other mammalian subject. A method according to this aspect of the invention desirably includes directing light into a structure generally in the form of a shell similar in form and size to a contact lens, desirably less than 3 mm thick, overlying the eye and dispersing the light within the structure so that the dispersed light passes out of the structure and into the cornea of the eye. For example, the step of directing light into the contact lens structure may include directing light into the structure through a transmission fiber connected to the contact lens structure. The light may be UV light, and the method may further include the step of applying a photo-activated cross-linking agent to the eye so that the cross-linking agent is present when the light passes into the eye. The method desirably further includes the step of allowing the subject to close his or her eyelids over the contact lens structure while the light is being applied.

Methods and apparatus according to certain embodiments of the invention can provide effective phototherapy, such as effective cross-linking, without requiring the patient to keep his or her eye open during the procedure, or to lie down facing a light source. This greatly enhances the comfort and practicality of the procedure. Moreover, the methods and apparatus according to these embodiments of the invention do not require the complex and expensive apparatus used to direct light into the eye heretofore.

BRIEF DESCRIPTION OF THE DRAWINGS

FIG. 1 is a diagrammatic perspective view depicting a component of a device in accordance with one embodiment of the invention.

FIG. 2 is a further diagrammatic perspective view depicting the component of FIG. 1 in conjunction with another component.

FIG. 3 is a diagrammatic partially sectional perspective view depicting the components of FIGS. 1 and 2 in conjunction with still further components of the device.

FIG. 19 is a diagrammatic, partially sectional view of a device according to a further embodiment of the invention.

FIGS. 20 and 21 are fragmentary sectional views of the device shown in FIG. 19.

FIG. 22 is a view similar to FIG. 20, but depicting a device according to yet another embodiment of the invention.

FIG. 23 is a fragmentary, diagrammatic sectional view depicting a portion of a device according to a further embodiment of the invention.

FIG. 24 is a diagrammatic sectional view depicting a device according to a still further embodiment of the invention.

FIG. 25 is a diagrammatic sectional view depicting a device according to yet another embodiment of the invention.

DETAILED DESCRIPTION

Figure 4:
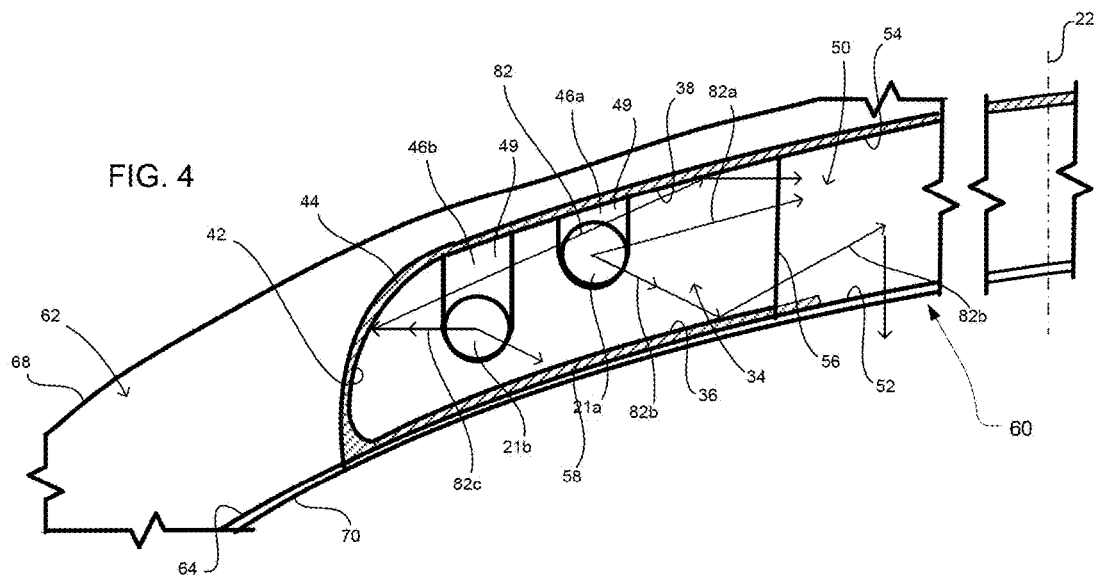
FIG. 4 is a fragmentary, diagrammatic sectional view depicting the components of FIGS. 1-3 in conjunction with still further components of the device.

A device according to one embodiment of the invention incorporates a first optically dispersive element in the form of a radially dispersive optical fiber 20 (FIG. 1). As used in this disclosure, the term "optically dispersive element" refers to an element that is adapted to scatter light propagating in a direction of propagation so that an appreciable portion of such light is redirected in directions transverse to the direction of propagation. The term "dispersive" is used herein interchangeably with the term "scattering", and has the same meaning as discussed in the foregoing sentence. The term "radially dispersive optical fiber" refers to a fiber, such as fiber 20, which is adapted to allow propagation of light along the length of the fiber while also scattering an appreciable portion of the light propagating along the fiber in directions transverse to the length of the fiber.

The degree of dispersion in an optical fiber can be stated in terms of its "extinction length." With respect to a fiber, the extinction length as referred to in this disclosure is the length along the direction of propagation in which light transmitted from a starting point along the length of the fiber loses 90% its power. Stated another way, the extinction length of a fiber is the length of fiber over which 90% of the incoming light is dispersed and thus emitted out of the fiber in directions transverse to the length of the fiber. Radially dispersive optical fibers having essentially any desired extinction length are available from sources including Corning Glass Works of Corning, N.Y., USA. As further discussed below, the desired extinction length depends in part on the length of radially dispersive fiber incorporated into the device. However, typical designs incorporate optical fibers having extinction lengths on the order of 0.5-4 meters.

Fiber 20 is arranged in one or more loops extending around a central axis 22. In the particular embodiment depicted, fiber 20 is arranged in a spiral of approximately two full turns constituting the loops. The inner turn 21a has an average diameter slightly larger than the diameter of an area of the cornea to be treated. Thus, the total length of fiber incorporated in the turns is about 25 mm. Most typically, the ratio of the length of radially dispersive optical fiber incorporated in the one or more loops to the extinction length of the optical fiber is 0.05:1 to 0.3:1, most typically about 0.2:1 to 0.3:1. As further explained below, the ratio is selected in conjunction with other design features to enhance the uniformity of light distribution achieved by the system.

The end 23 of the inner turn 21a is referred to herein as the termination end of the dispersive fiber. Termination end 23 is covered by a coating 25 adapted to absorb UV light. The outer end of the outer turn 21b constitutes the input end of the fiber in the loops. The radially dispersive optical fiber includes a short stub 24 extending out from the outer end of the outer turn 21b. Stub 24, and hence fiber 20, is connected to the distal end of a conventional, substantially non-dispersive transmission optical fiber 26 by a splice 28. For example, splice 28 may be a fusion splice made by fusing the ends of fibers 20 and 26 to one another or a mechanical coupling holding polished ends of the fibers in precise alignment with one another. Stub 24, splice 28 and transmission fiber 26 are referred to collectively as the input fiber system. The input fiber system may be covered with a conventional jacket or other protective element (not shown), so as to protect it from physical damage. However, the distal portion of the input fiber system adjacent the loops, including any jacket covering this portion of the fiber system, desirably is of relatively small diameter as, for example, 0.6 mm or less and more preferably 0.25 mm or less. As explained below, this helps to minimize irritation to the patient's eyelids in use of the device.

The proximal end of transmission fiber 26 is releasably connected to a UV light source 30, as by a conventional connector (not shown). Source 30 may be a conventional device such as a UV laser arranged to emit light at the desired wavelength for the therapy to be performed. Where the device is to be used in cross-linking of the cornea using riboflavin as a cross-linking agent, the light may be near UV light of 360 nm to 380 nm wavelength or blue light of about 425 nm to 475 nm wavelength.

The device further includes a fiber carrier 34 (FIGS. 2, 3) formed from a transparent material, preferably a polymer such as an acrylic. The fiber carrier is shown as opaque in FIG. 2 for illustrative purposes only. The transparent material of the fiber carrier will transmit UV light substantially without dispersion.

Fiber carrier 34 is generally in the form of a shallow dome with a concave interior surface 36, a convex exterior surface 38, and a hole 40 extending between the interior and exterior surfaces at the center of the dome. The fiber carrier 34 also defines a generally cylindrical edge surface 42 extending between the interior and exterior surfaces. As best seen in FIG. 4, the juncture between edge surface 42 and exterior surface 38 is provided with a radius 48 so that the edge surface 42 and exterior surface 38 merge gradually into one another.

The exterior surface 38 of the fiber carrier has a spiral groove defining an inner turn 46a and an outer turn 46b corresponding to the turns 21a and 21b of radially dispersive optical fiber 20. The outer turn 46b of the spiral groove terminates at an opening 48 extending through edge surface 42 of the fiber carrier. Turns 21a and 21b of fiber 20 are disposed in the turns 46a and 46b of the spiral groove, respectively. Thus, the axis 22 of fiber turns 21a and 21b also forms the central axis of the fiber carrier. The stub 24 of fiber 20 extends out of the fiber carrier through opening 48. A transparent filler 49 (FIG. 4) is disposed within the turns 46a and 46b of the groove. The filler defines surfaces that are flush with the exterior surface 38 of the fiber carrier. The features of the lens carrier, such as the edge surface 42 and the interior surface of hole 40, are substantially in the form of surfaces of revolution about the central axis 22.

The device further includes a mass 50 of an optically dispersive material disposed within the hole 40 in the fiber carrier 34. For example, mass 50 may be formed from a transparent silicone polymer having microscopic particles of an opaque, reflective material such as titanium, titanium dioxide, or zinc dispersed throughout the polymer. The dispersive properties of a material of this nature can be controlled by varying parameters such as the particle material, the ratio of particles to polymer, the size of the particles, and the shape of the particles.

Mass 50 is in the form of a dome-like shell having a concave interior surface 52 and a convex exterior surface 54. These surfaces generally conform to the dome-like configuration of the fiber carrier 34, so that the fiber carrier and shell 50 form a continuous dome-like structure having substantially smooth interior and exterior surfaces. Shell 50 also has a generally cylindrical edge surface 56 extending between surfaces 52 and 54 and abutting the inner surface of the fiber carrier 34, which defines hole 40. Shell 50 can be formed by casting it in place in the hole 40 of the fiber carrier while holding the fiber carrier in a mold defining the desired dome shape.

Shell 50 constitutes a second optically dispersive element. Here again, the degree of dispersion in such an element can be characterized by the extinction length of the element. This embodiment is intended to produce uniform irradiation intensity across the area of the cornea to be treated. In this case, the extinction length of the mass or shell 50 typically is greater than the diameter of the cylindrical edge surface 50.

A reflective element in the form of a film 58, best seen in FIG. 4, covers the interior and exterior surfaces 36 and 38 of the fiber carrier and also covers the edge surface 42 of the fiber carrier and the transition 44 between the edge surface and the exterior surface. For example, film 58 may be formed from aluminum or other metals. Film 58 also covers the entire exterior surface 54 of dispersive shell 50. Film 58 may extend beyond the edge surface 56 of the shell so that the film may cover a portion of the interior surface 52 of the dispersive shell remote from the central axis 22 of the device. However, a portion of the interior surface 52 adjacent the axis is left uncovered by the metallic film 58, so as to define an aperture 60 surrounding axis 22. As best appreciated with reference to FIG. 4, the reflective element 58 forms a cavity, and the dispersive mass 50 is disposed within this cavity. The reflective element 58 includes a reflective circumferential surface overlying the edge surface 42 of the wafer carrier and extending around axis 22. This reflective circumferential surface is in optical communication with the edge surface 56 of mass 50, through the clear fiber carrier 34. The reflective element 58 also includes a surface facing in an inward direction, toward the bottom of the drawing, overlying the outer surface 54 of mass 50, as well as an outwardly facing ledge surface overlying the inner surface 36 of the fiber carrier.

This embodiment is intended to correct myopia by flattening the cornea. For this purpose, the aperture is generally circular and has a radius approximately equal to the radius of a portion of the cornea to be treated. The aperture size appropriate for the particular patient is selected by the ophthalmologic professional. That is, aperture 60 is sized to cover only a portion of the cornea adjacent the center of the cornea. As explained below, this will provide crosslinking near the center of the cornea, so as to treat myopia.

Film 58 may be on the order of a few microns to a few tens of microns thick. Merely by way of example, film 58 may be formed by conventional methods of depositing metals onto polymers as, for example, electroless plating followed by electroplating, vapor deposition, sputtering, or the like. Alternatively, the reflective metallic element may be formed by other metalworking methods such as stamping, die casting or machining.

The assemblage of the fiber carrier, radially dispersive fiber, dispersive shell, and reflective element is embedded in a housing 62. Housing 62 has a dome-like central portion defining a first interior surface 64 with a shape adapted to conform to the shape of the cornea. The housing also includes a skirt portion defining a second interior surface 66 surrounding the first interior surface. The second interior surface has a shape adapted to conform to the shape of the sclera or opaque portion of the eye surrounding the cornea. The assemblage of the fiber carrier 34 and shell 50 is mounted centrally in housing 62 so that the central axis 22 defined by the fiber and fiber carrier is coincident with the central axis of dome-like portion 64 of the housing. Housing 62 also has an exterior surface 68 extending generally parallel to the interior surface portions 64 and 66 and covering the exterior surfaces of fiber carrier 34 and shell 50. As best seen in FIG. 4, housing 68 includes a thin interior film 70 covering the interior surfaces of the fiber carrier 34 and shell 50 and overlying metallic film 58 on the interior surface of the fiber carrier. Housing 62, apart from interior film 70, may be formed from essentially any material, but typically is formed from a relatively soft polymer such as silicone. Interior film 70 desirably is formed from a material having good compatibility with the tissues of the eye as, for example, a hydrophilic polymer. The material of film 70 should also be capable of transmitting the light to be applied.

Figure 5:
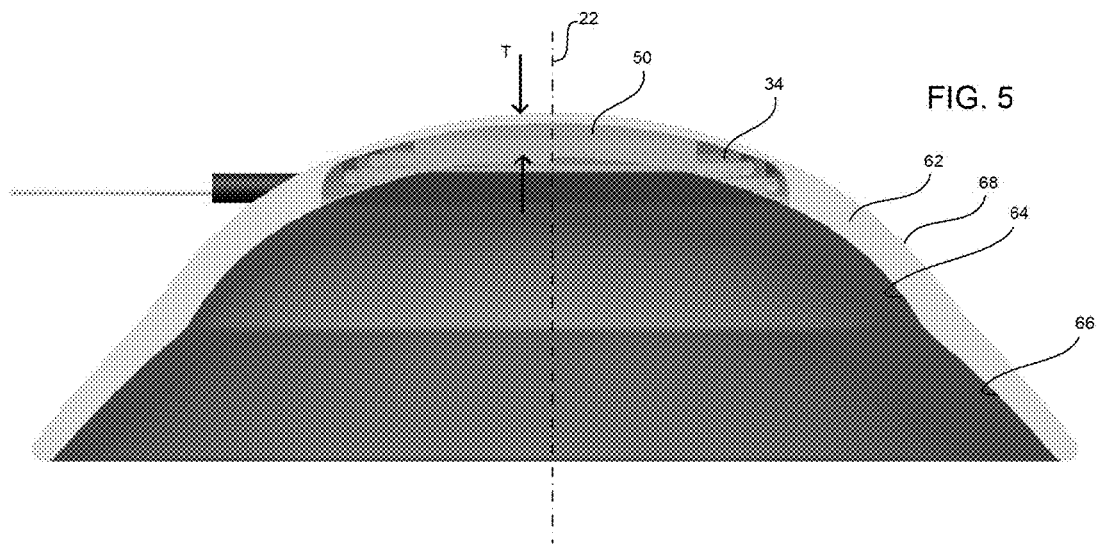
FIG. 5 is a diagrammatic sectional view depicting the device incorporating the components of FIGS. 1-4.

As best appreciated with reference to FIG. 5, the housing 62, fiber carrier 34, and shell 50 cooperatively form a contact lens structure substantially in the form and shape of a conventional scleral fit contact lens. Thus, the entire structure forms a relatively thin shell having interior and exterior surfaces generally conforming to the shape of the cornea and sclera. The thickness T of the entire contact lens structure desirably is no more than 3 mm, preferably no more than 2 mm, more preferably less than 1 mm, and most preferably less than 800 μm.

Figure 6:
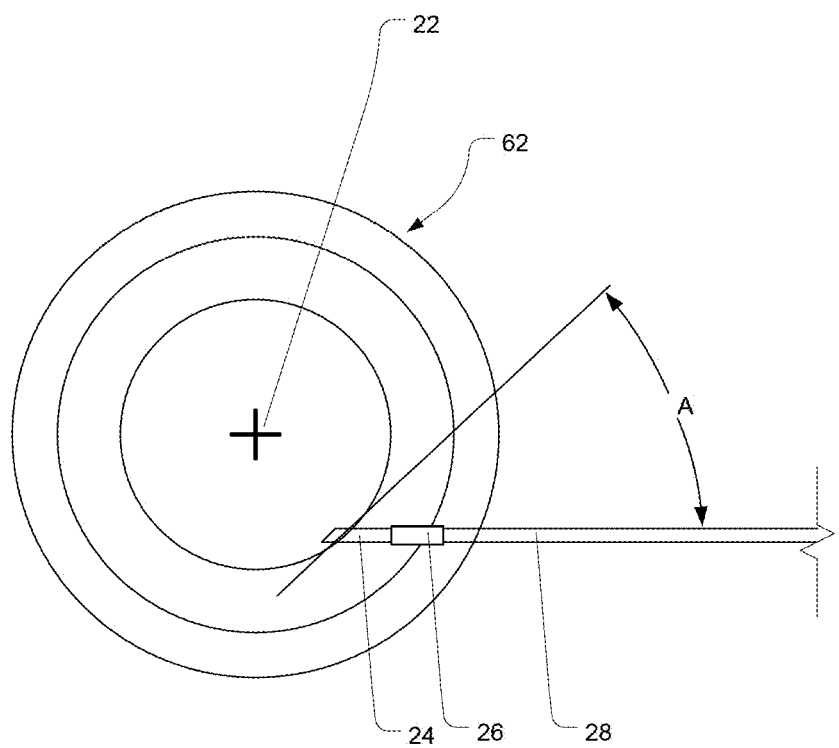
FIG. 6 is a diagrammatic plan view depicting the device of FIG. 5.

As best seen in FIG. 6, the fiber system (stub 24, transmission fiber 26 and splice 28) extends out the housing 28 in a direction transverse to the central axis 22. The fiber system exits the housing at an angle A relative to a line tangent to a circle concentric with central axis 22 and passing though the exit point. Angle A may have any value, including 0°, such that the fiber system exits parallel to the tangent line, and 90°, such that the fiber system exits perpendicular to the tangent line. Typically, an angle between 0° and 90° is chosen to mitigate both manufacturing challenges and contact with the patient's eyelid during the use of the device.

Figure 7:
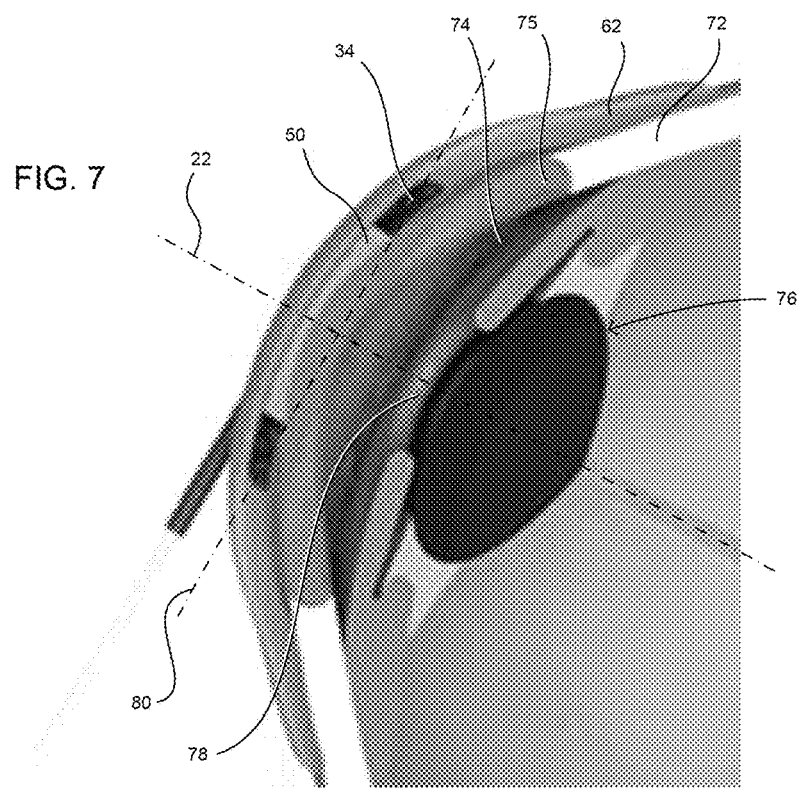
FIG. 7 is a diagrammatic sectional view depicting the device of FIGS. 1-5 in conjunction with a human eye.

In a method according to a further embodiment of the invention, a device as discussed above with reference to FIGS. 1-6 is placed over the front surface of the eye of a human or other mammalian subject as depicted in FIG. 7. The interior surfaces of the housing 62, fiber carrier 34, and dispersive shell 50 overlie the exterior surfaces of the sclera 72 and cornea 74 of the subject's eye. Typically, those portions of the device overlying the cornea are spaced slightly from the cornea so as to provide a small space between the outer surface of the cornea and the inner surface of the device. The central axis 22 of the device is substantially aligned with the central axis of the subject's eye. The central axis of the subject's eye, as referred to in this disclosure, is the axis extending through the center of the cornea and the center of the lens 76 of the eye, as well as the center of the pupil 78 of the eye. In this orientation, the fiber turns 21a, 21b extend generally in planes transverse to the central axis of the eye, as indicated schematically by plane 80 in FIG. 6. Thus, the turns of the radially dispersive optical fiber extend generally parallel to the surface of the eye. Likewise, the interior and exterior surfaces of dispersive shell 50 extend generally parallel to the surface of the eye, and specifically the surface of the cornea. Also, the turns of the fiber surround the central axis of the eye, which, again, is substantially coincident with the central axis 22 of the device.

Before or during the application of the device to the eye, the eye is treated with a photo-reactive crosslinking agent 75 such as riboflavin and the crosslinking agent is allowed to permeate into the cornea 74. As seen in FIG. 7, the device may be used as a reservoir to trap the agent in contact with the cornea during permeation. After a the agent has permeated into the cornea, and before light is applied as discussed below, the agent desirably is removed from the space between the device and the cornea as, for example, by flushing this space with a liquid such as saline solution or the patient's natural tears. Alternatively, the agent may be confined in contact with the cornea by another device such as another contact lens shaped shell, which is removed and replaced by the device. Optionally the epithelial layer forming the outermost surface of the cornea may be removed or disrupted using conventional techniques so as to enhance permeation of the crosslinking agent into the collagen of the cornea.

While the crosslinking agent is present in the cornea, the light source 30 (FIG. 1) is actuated so as to direct light at a wavelength suitable for activating the crosslinking agent through the transmission fiber 26 and into dispersive fiber 20. Where the agent is riboflavin, the light may be near UV light of 360 nm to 380 nm wavelength or blue light of about 425 nm to 475 nm wavelength. The light enters through stub 24 of the dispersive fiber 20 and passes lengthwise along the fiber through turns 21a and 21b. Thus, the light passing along the dispersive fiber in turns 21a and 21b is directed generally parallel to the surface of the eye. As the light passes along the turns of the fiber, a portion of the light is dispersed from the fiber, and the dispersed portion propagates in directions transverse to the length of the fiber, as indicated by arrows 82 (FIG. 4). The light dispersed from the fibers passes through the transparent material of fiber carrier 34 into the dispersive shell 50 through the edge surface 56 of the shell. Some of the light dispersed by the fibers passes directly into the shell as indicated by arrow 82a in FIG. 4. Other light dispersed from by fiber passes into shell 50 by indirect paths, including one or more reflections from reflective film 58, as indicated by arrows 82b and 82c in FIG. 4. A substantial portion of the light directed into shell 50 through peripheral surface 56 is propagating in directions generally parallel to the interior surface 52 of the shell and thus generally parallel to the surface of the cornea. As used in this disclosure, a propagation direction can be considered "generally parallel" to a surface if the propagation direction forms an angle of less than about 45° and preferably less than 30° to the surface.

The light propagating through dispersive shell 50 is dispersed. Some of the light dispersed in the shell is directed in the inward direction, towards the inner surface 52 of the shell. This light passes through the aperture 60 (FIG. 4) and into the cornea 74. Of course, dispersion in shell 50 is omnidirectional, and some of the light dispersed by the material of the shell will travel in directions other than the inward direction. Light initially dispersed in the outward direction will be reflected back toward the cornea by the metallic film 58 overlying the outer surface. Light dispersed in directions parallel to the inner and outer surfaces of the shell may pass out of the dispersive shell 50, through the edge surface 56, and into the transparent material of the fiber carrier 34, but will be reflected back into the shell by film 58. Likewise, some of the light passing from the fibers into the dispersive shell 50 will travel entirely across the dispersive shell and out into the fiber carrier 34 at another location. This light also will be reflected back into the shell by film 58. Film 58 is not perfect, and some light will be lost during internal reflection. However, a substantial portion of the light dispersed by the fiber will ultimately pass out of the dispersive mass 50 through aperture 60 and into the cornea. The pattern of light travel discussed above is substantially symmetrical around the entire circumference of the device.

As the light passes from the inlet fiber 26 through the radially dispersive fiber 20, it diminishes in intensity. Accordingly, slightly less light will be dispersed from the fiber near the terminal end 23 of the fiber than near the input end and stub 24. However, this difference typically is minor. As pointed out above, the extinction length of the fiber is substantially greater than the length of fiber constituting turns 21a and 21b. Moreover, this difference is taken up over two full turns, i.e., 720° of travel in the circumferential direction around central axis 22. Thus, the circumferential non-uniformity is minimal. Moreover, the effects of the multiple reflections and multiple passes of light through the dispersive shell 50, as discussed above, compensate for any non-uniformity in the light dispersed from the fiber. Desirably, the light passing out from aperture 60 (FIG. 4) is of uniform intensity over the entire surface area of the aperture to within about 20% or less.

The system is actuated to provide a dose of light to the cornea sufficient to perform the desired crosslinking. Merely by way of example, a dose of about 5.4 Joules/cm$^2$ may be delivered over a period of about 30 minutes in a typical procedure. While the device is present in the subject's eye, the subject may close his or her eye and blink freely to provide hydration to the eye. The thin contact lens-like structure of the device allows the patient to do this without discomfort. When the patient closes the eye or blinks, the eyelids close over and around the distal portion of the fiber system. The small diameter of the fiber system limits any discomfort caused by the fiber. The patient's eyelids desirably are not held open by an ophthalmology speculum or other device. Moreover, the patient's head does not have to be retained in a fixed position during the procedure.

The device and procedure discussed above may be varied in many ways. In one such variant, the coating 25 on the termination end 23 of the fiber is reflective rather than light-absorbing. In this variant, light which reaches the termination end of the dispersive fiber is reflected back toward the input end. The reflected light is also dispersed by the fiber, so that the intensity of the reflected light diminishes as it travels toward the input end of the fiber. By contrast, the light originally supplied through to the fiber at its input end diminishes in intensity as it travels toward the termination end. These effects counteract one another to reduce non-uniformity in the amount of light dispersed along the length of the fiber.

The radially dispersive optical fiber used in the embodiments discussed above may incorporate any number of loops as, for example, a single loop or three or more loops. The turns 21a and 21b of the spiral dispersive fiber 20 discussed above form loops extending around the central axis of the device. In other structures, where multiple loops are desired, these can be provided as separate radially dispersive optical fibers.

The fiber carrier 34 and filler 49 discussed above with reference to FIGS. 3 and 4 may be replaced by a unitary mass of a clear material such as an epoxy or an acrylic which secures the dispersive fiber in one or more loops. The fiber may be embedded in the clear material as, for example, by casting the material around the fiber. In yet another variant, the clear material may serve as an adhesive so as to secure the fiber to another structural element of the device as, for example, the reflective element 58. In yet another variant, the fiber may be embedded in the dispersive mass. For example, in the embodiment discussed above, the dispersive mass 50 may include a peripheral portion which occupies the space remote from the central axis occupied by the fiber carrier 34 in FIGS. 3-5. The dispersive fiber loops may be embedded in this peripheral portion of the dispersive mass, so that a central portion of the dispersive mass is disposed inside the loops.

The skirt portion of the housing 62 defining the second interior surface 66 depicted in FIG. 5 may be omitted. In this variant, the device has the form and shape of a conventional corneal contact lens.

The embodiment discussed above with reference to FIGS. 1-7 is intended to provide substantially uniform light intensity over the entire aperture. However, an intensity gradient in radial directions, towards and away from central axis 22, may be provided by adjusting the properties of the dispersive mass. For example, the dispersive mass may have properties which vary with location within the mass as, for example, an extinction length which varies in the radial direction. In another example, the dispersive mass may be of uniform properties, but these properties may be selected to provide the desired gradient. For example, a mass having a short extinction length can produce a radial gradient.

Figure 8:
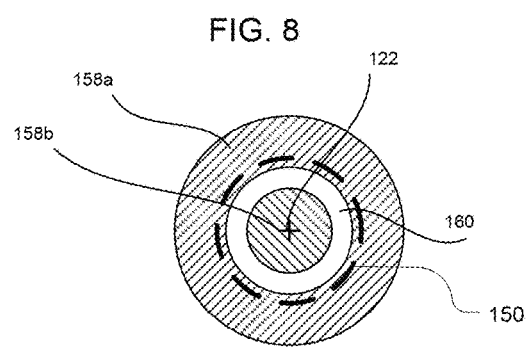
FIG. 8 is a diagrammatic plan view depicting a device in accordance with a further embodiment of the invention.

In the embodiment discussed above, light application and, hence, crosslinking occurs only over a central portion of the cornea. This tends to flatten the central portion and thus correct some or all of a patient's myopic error. A device according to a further embodiment of the invention (FIG. 8) has a dispersive shell 150 and other elements (not shown) similar to those discussed above with reference to FIGS. 1-6. However, the reflective film is patterned so that the aperture 160 is in the form of an annulus surrounding the central axis 122 of the device. Thus, the reflective film on the interior surface of the device includes a main portion 158a defining the outside of the annulus and a disc-like central portion 158b overlying a region immediately surrounding axis 122. This device may be used to treat hyperopia. Thus, the UV light will be applied to a ring-shaped zone of the cornea, remote from the central axis of the eye, the parameters of which are selected to optimize the corneal shape change, thus tending to increase the curvature of the cornea.

Figure 9:
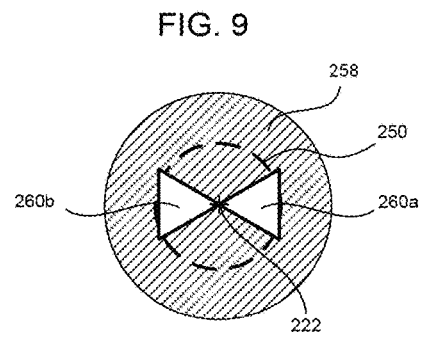
FIG. 9 is a view similar to FIG. 7, but depicting yet another embodiment of the invention.

A device according to yet another embodiment (FIG. 9) incorporates a dispersive shell 250 and associated fiber (not shown) similar to the corresponding elements of the device discussed above with reference to FIGS. 1-7. In this embodiment, however, the reflective film 258 is patterned so as to provide an aperture that is non-uniform in the circumferential direction around axis 222. In the particular embodiment shown, the aperture 260 includes two generally triangular, diametrically opposed portions, so that the aperture as a whole defines a "butterfly" shape. A structure according to this embodiment can be used to treat astigmatism. In this embodiment, the device is positioned on the eye so that the butterfly shape corresponds to a particular region of the eye where UV light application and crosslinking are desired. To aid in this process, the exterior surface of the device may have a mark indicating the orientation of the butterfly-shaped aperture. Also, the device may have a weight or other element to aid in maintaining the desired orientation during the treatment. Alignment also may be controlled by where the on the circumference of the device the fiber exits and the exit angle A discussed above with reference to FIG. 6.

Figure 10:
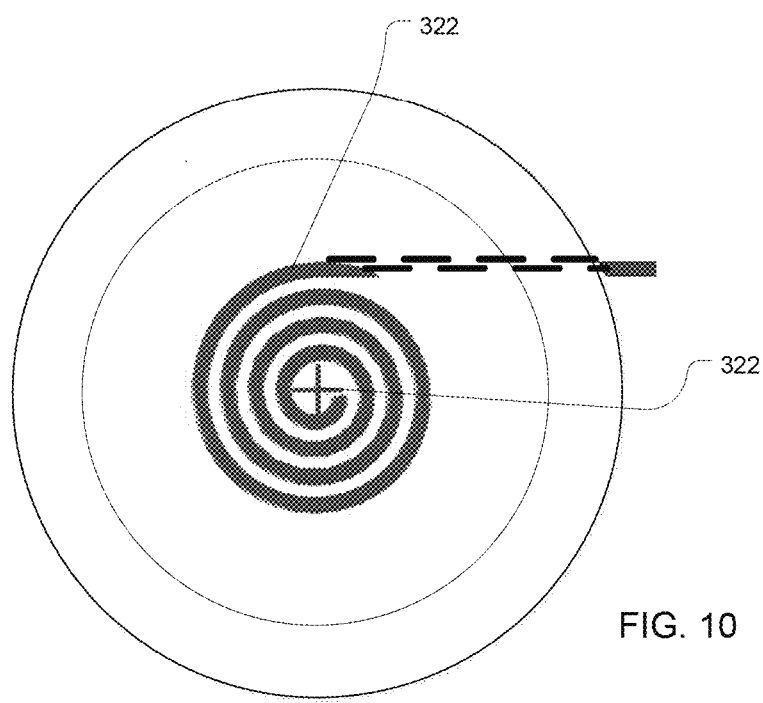
FIG. 10 is a diagrammatic plan view depicting a device according to yet another embodiment of the invention.
Figure 11:
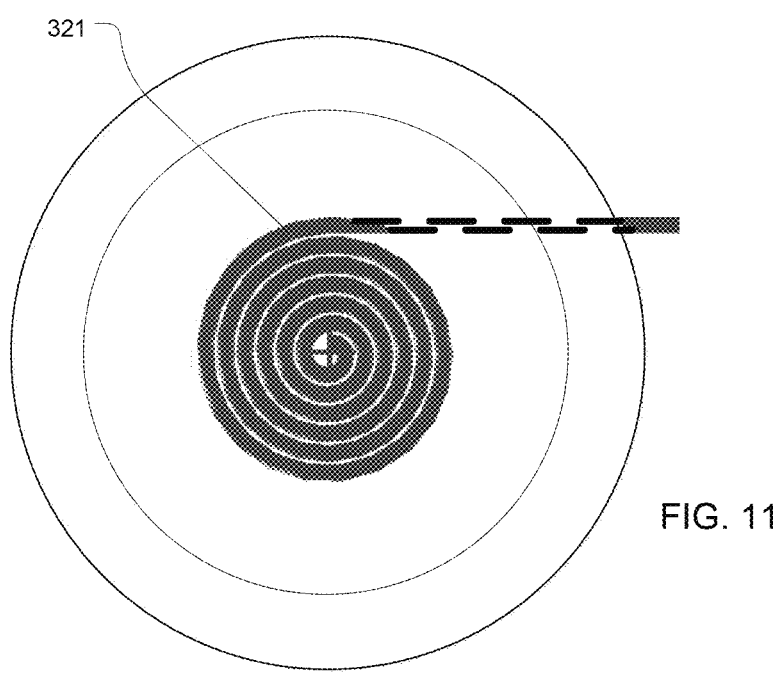
FIG. 11 is a diagrammatic plan view of a device in accordance with yet another embodiment of the invention.

A device according to a further embodiment of the invention (FIG. 10) includes only one optically dispersive element in the form of a radially dispersive optical fiber 320. The dispersive fiber 320 may be arranged in the form of a spiral extending around the central axis 322 of the housing. As in the embodiments discussed above, housing 362 may have the form and size of a scleral contact lens or a corneal contact lens. The spiral fiber may be disposed along a generally dome-like or disc-like surface of the housing extending transverse to the central axis 322 of the housing 362 of the device and facing toward the inner side of the housing. A reflective element (not shown) may be interposed between the fiber and the housing. The fiber may be secured to the housing surface or to the surface of the reflective element by a clear adhesive. In this arrangement, light dispersed from the fiber may pass directly into the cornea without passing through another optically dispersive element. In another arrangement, one or more optically dispersive layers (not shown) may be provided. For example, the adhesive that secures the fiber to the housing or reflective element may be optically dispersive. The dispersive adhesive may be disposed between turns of the spiral, and also may form a layer covering the fiber spiral on the side facing toward the eye. Alternatively or additionally, one or more other dispersive layers may be provided between the fiber and the eye. As depicted in FIG. 11, a more uniform light distribution can be achieved by reducing the spacing between turns of the spiral 321. The turns of the spiral may touch one another to form a solid fiber mat. In these embodiments as well, light propagating along the fiber passes in a direction generally parallel to the surface of the eye, and the light that reaches the eye is light dispersed out of the fiber through the side walls of the fiber. The embodiments of FIGS. 10 and 11 are arranged to treat a circular region around the central axis. In a further variant, the spiral dispersive fiber may extend only within an annular region so as to treat an annular region of the cornea. In yet another variant, the dispersive fiber may be arranged to provide illumination only within regions of other shapes and sizes as, for example, a "butterfly-shaped" region as discussed above with reference to FIG. 9.

A device according to yet another embodiment of the invention (FIG. 12) includes an optically dispersive mass or shell 450, similar to the optically dispersive shell 50 discussed above with reference to FIGS. 3-6. In this embodiment, the edge surface of the dispersive shell is surrounded by an array of LEDs 402 adapted to emit UV light. Light emitted by the LEDs passes into the optically dispersive shell 450 through the edge surface 456 of the shell in much the same way as light dispersed by the fiber in the embodiment discussed above with reference to FIGS. 1-7. Merely by way of example, the LEDs 402 may be mounted within a clear polymer diode carrier 434 generally similar to the fiber carrier 34 discussed above. Desirably, the diode carrier 434 and shell are equipped with a reflective element (not shown) similar to that discussed above, covering the outer surface of the shell 450, facing away from the eye, and also covering the periphery and inner and outer surfaces of the diode carrier 434. The diode carrier and shell are mounted in a housing 462 similar to that discussed above. The LEDs are powered by a simple electric circuit schematically indicated at 404. Circuit 404 may be connected to power and ground wires 406. In this embodiment as well, the entire structure desirably has shape and dimension similar to that of a conventional contact lens and, thus, desirably has a maximum thickness similar to that discussed above. The device may be placed in the eye of the subject with the wires extending out of the subject's eye between the eyelids. Here again, the subject may close his or her eye during the procedure. Alternatively, the LED's may be powered by wireless power transmission as discussed below.

Figure 13:
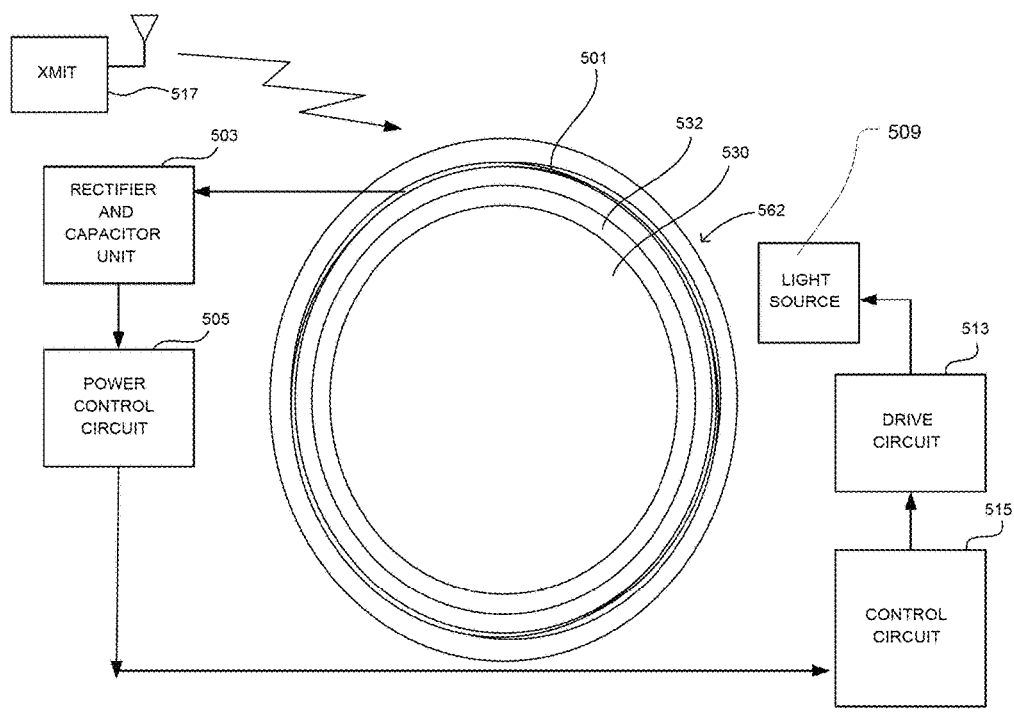

A device according to yet another embodiment of the invention (FIG. 13) includes a housing 562 in the form of a contact lens similar to the housings discussed above. The device of FIG. 13 further includes an antenna 501 on or within housing 562. The antenna, which may be in the form of a coil consisting of wire loops or tin oxide deposition for example, forms a near-field resonant tank circuit. For power transfer, the antenna is linked to a rectifier and storage capacitor unit 503, which, in turn, is electrically connected to a power control circuit 505. Power control circuit 505 provides regulated power voltages to other elements of the system. The structure further includes an illuminating element 530 adapted to apply light to the cornea as discussed above. For example, the illuminating element may include a dispersive structure connected to a source of light external to the housing by a transmission fiber as discussed herein in connection with FIGS. 1-11 and 19-25, or a dispersive element and an LED array mounted on or in the housing as discussed above in connection with FIG. 14.

A sensing element 532 is in optical communication with the illuminating element so that light from the illuminating element impinges on the sensing element. The sensing element is adapted to generate one or more signals which represent the light impinging on the sensing element, and thus represent the light applied by the illuminating element.

Figure 14:
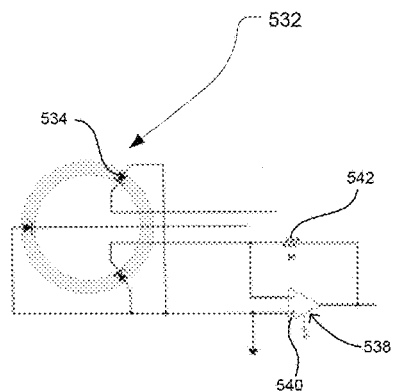
FIG. 14 is a schematic diagram of a component used in the device of FIG. 13.

One form of sensing element 532 is depicted in FIG. 14. This sensing element includes one or more photosensors such as PIN diodes 534 sensitive to UV light mounted in a ring 536. The ring is mounted on the housing 562 so that the ring structure encircles the dispersive mass included in the illuminating element 530. For example, where the illuminating structure incorporates a fiber carrier and reflective element as discussed above with reference to FIGS. 1-7, the ring structure may be disposed within the reflective element and extend around the fiber carrier or between the fiber carrier and the dispersive mass. The ring structure may be integral with the fiber carrier. Where the illuminating structure includes a diode carrier and LED array as discussed above with reference to FIG. 12, the ring structure may encircle the diode carrier, or may be integral with the diode carrier, and some of the LEDs included in the array may be connected to act as the photosensors of the sensing element rather than as light emitters. The sensing element may include one or more signal processing circuits 538. In the particular embodiment shown, the signal processing circuits

538 include three current-to-voltage converters, each incorporating an amplifier 540 and feedback resistor 542. Only one of these converters is depicted in FIG. 14 for clarity of illustration.

The device further includes an analog drive circuit 513 (FIG. 13) arranged to supply power to the light source 509 associated with the light emitting element 520. For example, where the light-emitting element includes an LED array, the drive circuit 513 supplies power to the LEDs. Where the light-emitting element includes an external light source such as a laser connected to a transmission fiber, the drive circuit supplies power to the laser. Drive circuit 513 has a set point value input connected to a control circuit 515. The control circuit has one or more inputs connected to sensing element 511. In some embodiments, all of the foregoing components can be are mounted on housing 562. In other embodiments, the control architecture (circuits 513 and 515) is located remote from the housing 562 and communicates with the photosensor(s) of sensing element 530 either through fine wires the run between the lens and the control system, or wirelessly. For wireless communication, a telemetry transmitter (not shown) may be mounted on the housing and connected to antenna 501 or to another antenna mounted on or in housing 562. The device further includes a radiofrequency ("RF") transmitter 517 separate from housing 562.

In operation, RF power as, for example, at about 100 kHz, is supplied by transmitter 517 through near field communication with antenna 501. The power received by antenna 501 is rectified by rectifier 503 and conditioned by power control circuit 505. The power control circuit 505 supplies power to the other electronic elements which are mounted on the housing as discussed above. The signal or signals from sensing element 532 will represent a proxy proportional to the amount of light available for UV corneal crosslinking and serves to aid in dosimetry. During delivery of the UV, control circuit compares the applied UV intensity represented by this photodetector generated signals to a signal representative of the desired applied intensity. The control circuit 515 desirably incorporates a calibration memory incorporating data representing the correlation between the signal or signals from the sensing element 532 and the actual dose applied to the subject's eye. The control circuit 515 varies the set point control signal applied to the control unit 513 so as to maintain the applied intensity at the desired level.

In a further variant, an additional intensity sensor (not shown) is located at a light source such as a laser external to the housing. In this variant, the sensing system will not only be able to control the applied intensity, it can also serve as an error or damage detector. Unaccounted for differences between launched optical power supplied by the light source and optical power detected by the sensing element are likely due to damage to the fiber system or to a lens or other optical element.

The concept of monitoring of applied dose discussed above with reference to FIG. 13 also may be applied to the other embodiments discussed above. For example, the embodiment discussed above with reference to FIGS. 1-6 may be provided with a sensing fiber. The sensing fiber may be connected through an output fiber extending parallel with transmission fiber to a diode or other photodetector mounted outside of the device housing as, for example, at the UV light source. Control circuitry responsive to the signal from the photodetector also may be mounted outside of the housing.

A device in accordance with a further embodiment of the invention (FIG. 15) includes a contact lens-like structure 600, which may be similar to any of the structures discussed herein. In addition, the device includes pairs of electrodes 601 adapted to overlie the patient's eye outside of the region to be treated. For example, the electrodes 601 may be fastened to the housing of the device so that the electrodes are exposed at the inner surface of the housing which faces toward the eye during use. Merely by way of example, the electrodes may be formed from materials such as tin oxide, or noble metals such as gold and silver. As discussed below, the electrodes are used as liquid level sensors to help maintain a constant liquid presence in the space between the device and the patient's eye. The pairs of electrodes are distributed over the circumference of the contact lens structure. In the particular embodiment illustrated, three pairs of electrodes are equally spaced around the circumference. The electrodes of each pair desirably have a known conductive surface area presented to the space and are spaced from one another by a calibrated distance $D_E$. For example, the electrodes may be 0.03 inches (0.77 mm) diameter with 0.125 inches (3.2 mm) center-to-center spacing. In some cases, the inner surface of the housing is coated with a hydrophilic layer to aid the adhesion of the device to the eye. This hydrophilic layer can hold a layer of conductive fluid over the surfaces of the electrodes. Such layer may be sufficiently thick so that the impedance of the retained layer will approximate the impedance of a liquid present in the space between the housing and the eye. To prevent this, the hydrophilic layer may be omitted in areas 602 of the inner surface carrying the electrodes.

The device according to this embodiment further includes a port 603 communicating with the interior surface of the housing, so that the port is open to the space between the device housing and the patient's eye during use. Port 603 is connected to a liquid supply conduit 605, so that the conduit communicates with the interior surface of the contact lens structure. Supply conduit 605 may be a small-diameter capillary conduit. The supply conduit 605 may extend alongside of the transmission fiber supplying light to the device. The supply conduit 605 may be a tubular fiber, such as a pipette or polyimide tube. In some embodiments, the conduit may additionally serve as the transmission fiber. Supply conduit 605 is connected to a pump 607. Pump 607 is connected to a source 609 of a liquid to be applied prior to and/or during treatment depending on treatment protocol.

Each pair of electrodes 601 serves as an individual impedance measuring element to acquire individual measurements. The pairs of electrodes desirably do not interact with one another through leakage current paths. To accomplish this, each pair of electrodes 601 is connected to an individual sensor circuit 610.

Figure 16:
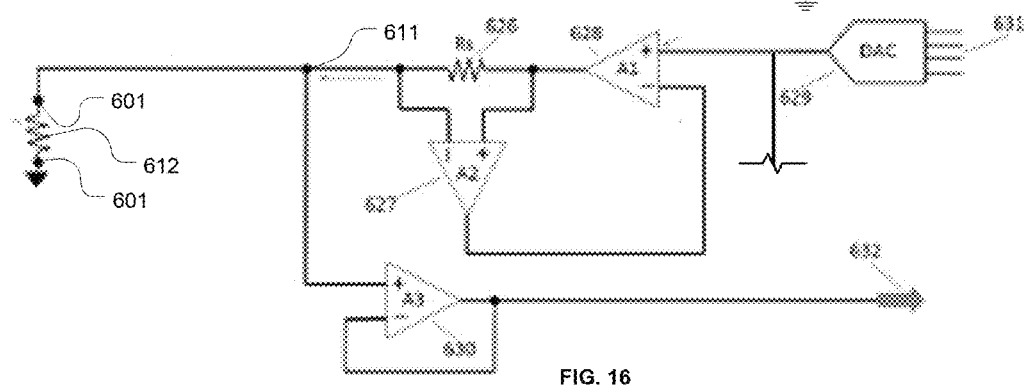
FIG. 16 is a circuit diagram of an element used in the device of FIG. 15.

A single one of the sensor circuits 610 is shown in FIG. 16. It includes an error amplifier A1, 628 that has one input connected to digital to analog converter ("DAC") 631. The output of error amplifier 628 is connected through a current sense resistor Rs, 626 to one electrode 601 of a pair. The opposite electrode of the pair is connected to ground. The impedance between the electrodes is shown schematically at 612. An amplifier A2, 627 has inputs connected on opposite sides of current sense resistor 626. The output of amplifier A2, 627 is connected to the other input of error amplifier A1, 628. A dedicated precision analog amplifier stage A3, 630 is connected to a circuit node between the current sense resistor 626 and the electrode pair. In operation, error amplifier 628 receives a current set point signal from DAC 631 and maintains the current passing through the current sense resistor at a constant level such that the output from amplifier A2, 627 is equal to the set point signal. The voltage at node 611 and the output signal 632 from amplifier stage A3, 630 thus represent the impedance 612 between the electrodes of the pair.

Figure 15:
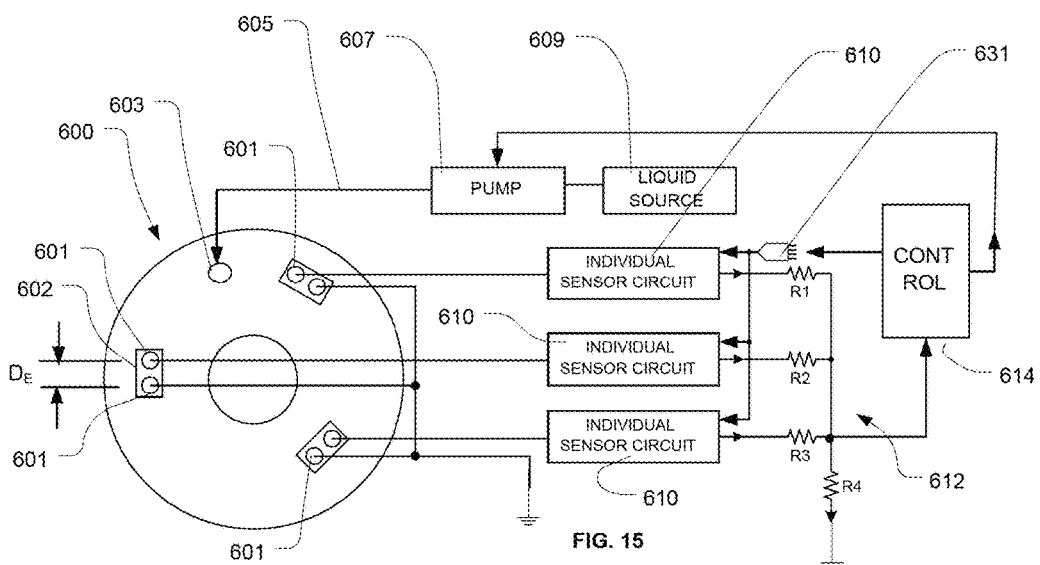
FIG. 15 is a schematic depiction of a device according to a further embodiment of the invention.

As seen in FIG. 15, the DAC 631 may be common to all of the sensor circuits. The output signals 632 from the individual sensor circuits are combined with one another by an analog summing circuit 613, and the combined signal is supplied to a control circuit 614. This combined signal will vary with the degree of hydration of the space between the lens-like structure and the eye. The control circuit controls pump 607 so as to maintain the desired hydration. The sensor circuits and control circuits may be disposed outside of the contact lens structure, with the sensor circuits connected to the electrodes 601 with a simple multi-wire interface Alternately, the signal processing may be contained "on lens" by utilizing a localized silicon IC or ASIC.

Figure 17:
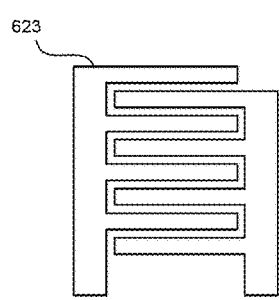
FIGS. 17 and 18 are diagrammatic plan views of elements used in further embodiments of the invention.
Figure 18:
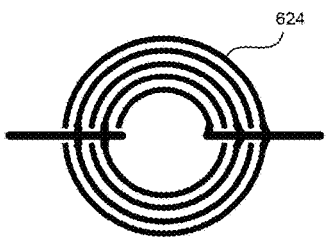

Other sensing elements may be employed, such as an interdigitated finger array 623 (FIG. 17) or circular interdigitated arrays 624 (FIG. 18). The element's measurement of impedance may be by means of either a μA (microampere) precision DC current or, alternately, a kilohertz range, AC excitation. AC excitation is typically employed in most "wetted" measurement applications.

In other embodiments, multiple sensing elements such as multiple electrode pairs are placed on the inside surface of the device, exposed to the space between the device and the cornea. When this space is filled with a conductive solution, all sensing elements register the same impedance. As fluid drains or leaks out of the space, the impedances of various elements will deviate from one another. This deviation is used as a control signal to cause the pump to infuse additional fluid until the impedances of the sensors register that each is bathed in fluid.

In some embodiments, the sensing elements are not electrodes, but mechanically resonant elements. A shift in the measured resonant frequency or mechanical impedance can be used as a pump control signal in place of a shift in the electrical impedance discussed previously.

Figure 12:
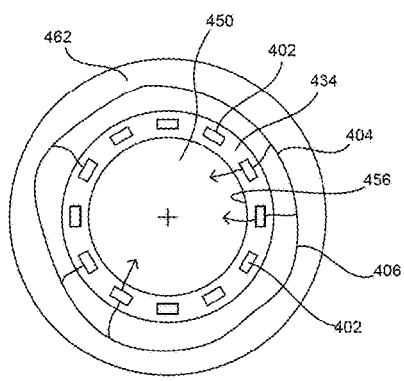
FIGS. 12 and 13 are diagrammatic, partially schematic block-diagram depictions of devices in accordance with still further embodiments of the invention.

The feedback control system shown in FIG. 12 can be varied and, indeed, in some embodiments, can be omitted. Thus, liquid can be supplied under pressure through conduit 605 without any feedback control.

Embodiments of the invention that incorporate a fluid sensing system can be employed in one method of the corneal collagen crosslinking procedure whereby the device is placed on the eye during the preparation phase of the procedure, and a photoactive agent containing solution is pumped into the space between the lens and the cornea to enable corneal saturation with the photoactive agent such as riboflavin. The sensing systems ensure the reservoir is full throughout this saturation phase. After sufficient time, the pump is activated to deliver a wetting solution without riboflavin to flush the reservoir space, as any riboflavin in this space will prevent some of the UV from reaching the cornea. Once flushed, the pump and sensing system then maintains a wet corneal surface throughout the UV delivery phase.

A device according to a further embodiment of the invention (FIGS. 19-21) includes an optical structure 700 that incorporates a reflector 702. Reflector 702 includes an inner element 704 that defines a first interior surface 706 in the form of a surface generally corresponding to the shape of the cornea and having a central axis 722. The interior element additionally defines an aperture 710, which, in this instance, is a circular aperture concentric with axis 722. The interior element has a reflective circumferential surface 712 in the form of a cylinder concentric with axis 722. The interior element 704 also has a ledge surface 714 extending from the aperture 710 to the circumferential surface 712. Ledge surface 714 faces in the outward direction (towards the top of the drawing in FIG. 21), as indicated by the arrow O. Ledge surface 714 desirably also is a reflective surface.

Reflector 702 further includes an outer element 716 overlying the outward extremity of the inner element 704. Outer element 716 is shown in transparent, phantom view in FIG. 19 for clarity of illustration. The outer element is secured to the inner element as, for example, by interlocking ridges 718 at the periphery of these elements, remote from axis 722. The outer element 716 defines a reflective surface, referred to herein as the "cap surface" 720, extending across axis 722 and spaced apart from ledge surface 714. Reflector 702 thus defines a cavity 724 (FIG. 21) communicating with aperture 710. The cavity is bounded in part by the circumferential reflective surface 712 and the reflective cap surface 720 and.

The reflective surfaces 712, 720, and 714 of the reflector may be arranged to provide either specular reflection or diffuse reflection. For example, the elements of the reflector may be formed from a metal such as aluminum with polished surfaces to provide specular reflection or with roughened surfaces to provide diffuse reflection. Alternatively, the elements of the reflector may be formed form a material such as a polymer coated with a metal such as aluminum. In yet another arrangement, the reflective surfaces may be formed by materials that provide a highly efficient diffuse reflection in the wavelengths to be applied. For example, films suitable for providing diffuse reflection of ultraviolet and blue light are commercially available from the 3M Company of Minneapolis, Minn. USA.

An optically dispersive element 726, such as a mass of a dispersive composition as discussed above, is disposed within cavity 724. The dispersive element is generally in the form of a disc concentric with axis 722. It has an outer surface 728 facing outwardly and confronting the cap surface 720 of the reflector and an inner surface 730 facing inwardly. The inner surface includes a portion overlying ledge surface 714 of the reflector, as well as a portion extending across aperture 710. This portion of the inner surface projects into the aperture so that it defines a surface region continuous with the first inner surface 706 of the reflector. The dispersive element 726 also defines an edge surface 732, which is in the form of a cylinder concentric with axis 722. The diameter of edge surface 732 is slightly smaller than the diameter of circumferential surface 712 of the reflector, so that the dispersive element and reflector cooperatively define an annular gap 734 extending around the dispersive element. Gap 734 is filled with a clear material, which may be a solid or gel, a liquid, or a gas such as air. The edge surface 732 of the dispersive element is in optical communication with the circumferential surface 712 of the reflector.

The reflector further defines a bore 740 (FIGS. 19, 20) extending through the inner and outer elements in a plane transverse to the central axis 722. In the particular embodiment depicted, the bore 740 extends in a plane perpendicular to the axis. Bore 740 communicates with the interior of cavity 724 and, in particular, with gap 734. As best seen in FIG. 20, bore 740 communicates with the cavity and gap at a location near to the reflective circumferential surface 712. A transmission optical fiber 742 extends through the port 740 and is held in place by a coupler 744 in the form of a sleeve that surrounds the fiber. The coupler 744 is secured to the fiber and to the internal wall of bore 740 as, for example, by an adhesive.

Fiber 742 has a distal end 746 and a proximal end (not shown). The proximal end is equipped with an appropriate coupler (not shown) for engagement with a light source such as light source 30 (FIG. 1). The distal end 746 extends coaxially with bore 740 and thus extends in a plane transverse to and preferably perpendicular to axis 722. The distal end 746 of the fiber is positioned within gap 734 adjacent the circumferential reflective surface 712. As seen in FIG. 20, viewing the distal end of the fiber in a plane transverse to the axis, the distal end of the fiber may extend in a direction that is tangential to the circumferential surface 712 or that lies at an angle $A_{DE}$ to such a tangent.

The optical structure 700, including the reflector and dispersive element, is mounted in a housing 762. As best seen in FIG. 19, the housing 762 may encompass a portion of the fiber 742 and coupler 744 extending out of the reflector. As in the embodiments discussed above, housing 762 is a generally shell-shaped structure, desirably less than 3 mm thick, having an interior surface generally conforming to the shape of a surface of the eye. For example, the housing 762 may have a first interior surface portion 764 that constitutes a continuation of the first interior surface 706 defined by the reflector and by the inner surface of dispersive element 726, so as to form a composite first interior surface generally conforming to the shape of the cornea of the eye. In the particular embodiment depicted, housing 762 further includes a second interior surface portion 766 corresponding to the shape of the sclera of the eye. Here again, the assembly including the optical structure 700 and housing 762 forms a thin shell having an interior surface corresponding to the shape of the eye, so that the entire structure is generally of the form and size of a conventional scleral contact lens. As discussed above, the second surface portion 766 may be omitted so that the entire structure will have the form and size of a conventional corneal contact lens. Here again, the interior surfaces of the housing and of the optical structure may be covered with a film of a hydrophilic material (not shown).

In operation, the assembly is positioned on the eye with the inner surfaces overlying the corresponding surfaces of the eye in much the same manner as discussed above with reference to FIG. 7. In this condition, the inward direction of the optical assembly constitutes the direction toward the eye of the patient, whereas the outward direction is the direction away from the eye of the patient. Aperture 710 is aligned with the region of the cornea to be treated.

While the assembly is in this position, light is directed into cavity 724 through the transmission fiber 742. Light passes from the distal end 746 of the fiber, strikes the reflective circumferential surface, and is reflected along a path around the periphery of the dispersive element. This path is schematically indicated in part by the path L in FIG. 20.

The light path L depicted in FIG. 20 is simplified for purposes of illustration. For example, the light may be refracted as it passes between the gap 734 and the dispersive element 726. Depending upon the indices of refraction of the medium in gap 734 and the dispersive element, the interface between the dispersive element and the gap may serve to confine the light to within the gap, so that the dispersive element and the circumferential reflective surface 712 serve as an annular light guide to help direct the light around the circumference of the structure.

As the light propagates around the structure, some of the light will be directed inwardly, toward axis 722. Some of the light will be spread in the inward and outward directions (FIG. 21) and thus may encounter the reflective cap surface 720 (id.) and the reflective ledge surface 714. In general, the light propagates inwardly towards the central axis 722 and thus travels in directions generally parallel to the inner and outer surfaces of the dispersive element. As in the embodiments discussed above, the light passing through the dispersive element is dispersed in directions transverse to the inner and outer surfaces of the element, so that some of this light is dispersed in the inward direction and exits through aperture 710 into the eye. In the manner discussed above, the light performs the desired therapy as, for example, cross-linking of the collagen in the cornea. As in the embodiments discussed above, the eye desirably is treated with a cross-linking agent.

The embodiment discussed above with reference to FIGS. 19 and 20 provides several significant advantages. It avoids the cost and complexity associated with the dispersive optical fiber. There is no need for a splice between the transmission fiber 742 and a dispersive fiber. Moreover, because the transmission fiber is optically coupled directly to the interior of the cavity and directly to the dispersive element 726, without passing through any other dispersive element light transmitted along the transmission fiber will be efficiently coupled into dispersive element 726. The structure according to this embodiment also provides advantages in patient comfort and ease of therapeutic applications similar to those discussed above. Here again, the patient need not hold his or her eye open during the procedure and desirably may close or blink his or her eye freely.

An optical structure 800 used in a further embodiment of the invention is schematically depicted in FIG. 22. This structure is identical to the optical structure 700 discussed above with reference to FIGS. 19-21. However, in structure 800, the dispersive element 826 has a diameter equal to the diameter of the reflective circumferential surface 812, so that the edge surface 832 of the dispersive element is in contact with the circumferential reflective surface. Also, in this embodiment, the distal end 846 of the transmission optical fiber is disposed within the dispersive element, near the edge surface 832 and circumferential surface 812. Placing the distal end of the optical fiber within the dispersive element facilitates efficient optical coupling of the light emanating from the transmission fiber into the dispersive element. In the particular embodiment shown, dispersive element 826 has a graded composition. It has low dispersion (long extinction length) in a peripheral region 827 disposed remote from axis 822, near the edge surface and near the circumferential surface 812 of the reflector, and has higher dispersion (shorter extinction length) in a central region 829 near axis 822 and thus near the aperture 810 of the reflector. As depicted, the gradation is stepwise. However, the gradation can be continuous.

The embodiments discussed above with reference to FIGS. 19-22 can be varied in numerous other ways. For example, the circumferential surface of the reflector, and the edge surface of the dispersive element need not be cylindrical surfaces. For example, they may be surfaces of revolution other than cylinders. In one embodiment, the circumferential surface of the reflector may be a conical shape so as to direct light reflected from this surface along a path having a component of direction in the inward or outward direction. For example, in the embodiment of FIGS. 19-21, the reflective surface may be arranged to direct the light with a component in the outward direction so that the light encounters the reflective cap surface 720, in the inward direction such that the light encounters the reflective ledge surface 714, or both. More complex surfaces of revolution such as a surface defined by a curve of arbitrary shape revolved around the central axis 722 may be employed. Indeed, the edge surface of the dispersive element and the circumferential surface of the reflector need not be surfaces of revolution. For example, these surfaces may be polygonal or of irregular shape. Individual portions of such surfaces may be tilted at arbitrary angles so as to reflect the light along trajectories having inward or outward components. Also, the cap surface 720 need not be planar and need not be contiguous with the outer surface of the dispersive element.

The transmission fiber need not be secured to the optical structure which includes the dispersive element. As schematically represented in FIG. 23, an optical structure 900 as discussed herein may include a feature such as a socket 902, and a transmission fiber 904 may have a distal end 906 arranged to mechanically engage with the socket 902 so as to place the distal end of the fiber in optical communication with the elements in the optical structure 900 that serves to disperse light. For example, in the embodiments of FIGS. 19-22, the socket would be arranged to hold the distal end of the fiber within the cavity of the reflector. In other embodiments, where a dispersive fiber is used, the socket and the distal end of the fiber would be arranged so that when the distal end of the fiber is engaged in the socket, the distal end of the fiber will be aligned with the dispersive fiber and in optical communication therewith. In the particular structure shown in FIG. 25, the distal end of the fiber is equipped with a collar 908 having a tapered exterior adapted to fit within a tapered interior defined by the socket 902. However, other mechanical configurations can be employed. For example, the distal end of the fiber may be bare, and the feature may define an opening adapted to engage the outside of the fiber directly, without any intervening collar or other structure. Other expedients for promoting optical coupling between the transmission fiber and other elements of the system can be used. For example, where the transmission fiber is to be coupled to a dispersive fiber, elements such as index-matching gels may be used to provide an optically efficient splice.

Use of a transmission fiber that is detachable from the optical structure and from the contact lens structure as a whole allows reuse of the transmission fiber with a different contact lens structure. For example, the contact lens structure may be used once and discarded so as to avoid the risk of infection, whereas the transmission fiber may be reused.

The optical structure need not be permanently mounted to a housing that helps in positioning the optical structure on the eye of the patient. As schematically depicted in FIG. 24, an optical structure 1000 is used in conjunction with a separate, detachable housing 1062. The optical structure 1000 may include any of the optical arrangements discussed above. Desirably, the optical structure 1000 includes the elements in the optical path between the transmission optical fiber 1002 and the aperture 1004, including one or more optically dispersive elements and, desirably, one or more reflective elements as discussed herein. Housing 1062 has one or more inner surfaces 1006 with a shape generally corresponding to the shape of a surface of an eye. For example, the inner surface 1006 may include a first surface having a shape generally corresponding to the shape of the cornea and may also include a second surface generally corresponding to the shape of the sclera as discussed above, or may include only the first surface. The inner surface 1006 defines an axis 1022, which extends towards and away from the eye when the inner surface 1006 overlies the surface of the eye. For example, axis 1022 may be aligned with the optical axis of the eye as discussed above. Housing 1062 also includes a wall 1008, which extends across the axis. Desirably, wall 1008 is arranged to transmit light at a wavelength to be applied to the eye. In the embodiments discussed herein, which are arranged to provide crosslinking, wall 1008 may be arranged to transmit light in the UV or blue wavelength bands.

The housing further includes a feature 1010 adapted to releasably engage optical structure 1000. In the embodiment depicted in FIG. 24, feature 1010 is shown as a simple tapered socket arranged to mate with a corresponding tapered wall on the outside of the optical structure 1000. However, feature 1010 may include any other element capable of engaging the optical structure as, for example, other forms of mechanical features capable of mating with corresponding mechanical features on the optical structure. Feature 1010 is arranged to hold the optical structure so that the aperture 1004 of the optical structure is aligned with axis 1022 and wall 1008 and so that the optical structure is separated from the eye E by wall 1008.

Desirably, housing 1062 is provided as a single-use device, whereas the optical structure 1000 is reusable. In a method according to a further embodiment of the invention, plural patients can be treated using the same optical structure. First, the optical structure with is assembled with a housing 1062. The assembly is placed over the eye of a first patient, so that the wall of the housing is disposed between the optical structure and the eye and so that the housing engages the eye and maintains the optical structure out of contact with the eye. The optical structure is then actuated as discussed above so that light is dispersed within the optical housing and passes out of the aperture 1004 and through the wall 1008 of the housing into the eye of the patient to perform the desired therapy. Following this step, the optical structure is disassembled from the housing and the foregoing steps are repeated using a different housing and, typically, a different patient on each repetition. The different housings may have different shapes or sizes to accommodate the needs of different patients.

A structure according to a further embodiment of the invention (FIG. 25) incorporates a dispersive element 1100 having an inner surface 1102 that faces inwardly toward the eye when the device is in place on the eye and an outer surface 1104 that faces outwardly away from the eye. The dispersive element has an axis 1122 extending through these surfaces. A transmission optical fiber has a distal end 1106 disposed on axis 1122 and spaced outwardly from the outer surface 1104. An optically transmissive medium 1107 is provided between the distal end of the fiber and the outer surface, so that the distal end of the transmission fiber is in optical communication with the outer surface 1104. The distal end of the fiber is equipped with one or more spreading structures schematically indicated at 1108. The spreading structures may include elements such as a mass of dispersive material, one or more reflectors, refractive elements, and configuration of the cleaved fiber end. Alternatively or additionally, the medium 1107 may have dispersive or refracting properties that serve to spread the light. The spreading structures are arranged to direct light supplied through the fiber away from axis 1122 so that the light impinges on an outer surface over a substantial region of the outer surface and desirably over the entire outer surface. The structure may further include a reflective element defining one or more of a circumferential reflective surface 1112 extending around the axis, an inwardly facing reflective cap surface 1114 disposed outward of the fiber distal end, and an outwardly facing reflective ledge surface 1116 facing the inner surface of the dispersive element.

As these and other variations and combinations of the features discussed above can be utilized without departing from the present invention as defined by the claims, the foregoing description of the preferred embodiments should be taken by way of illustration rather than by way of limitation of the present invention.

The invention claimed is:

1. A device for directing light to an eye of a subject comprising: a structure having an inner surface corresponding to the shape of an exposed surface of the eye, the inner surface of the structure facing in an inward direction, the structure incorporating an optically scattering mass in the form of a disc or dome having an inner surface facing in the inward direction, an outer surface facing in an outward direction opposite to the inward direction and an axis extending in the inward and outward directions, the mass having an edge surface extending in a circumferential direction around the axis, the structure further including a reflector defining a reflective circumferential surface extending in the circumferential direction around the axis and around the edge surface of the mass, the reflective circumferential surface facing toward the axis and toward the edge surface of the mass, the reflector further including a reflective cap surface facing in the inward direction and a reflective ledge surface facing in the outward direction, the circumferential surface, ledge surface and cap surface cooperatively defining a loop-shaped cavity extending in the circumferential direction around the axis, the device further including one or more optical fibers extending within the cavity in a direction transverse to the axis, the reflector capable of reflecting light emitted from the one or more optical fibers into the scattering mass toward the axis, the scattering mass capable of scattering at least a part of the light toward the eye.

2. A device as claimed in claim 1 wherein the one or more fibers includes an optically scattering fiber.

3. A device as claimed in claim 2 wherein the scattering fiber extends in at least one loop around the axis.

4. A device as claimed in claim 3 wherein the at least one loop is coaxial with the axis and the inner surface is arranged to position the structure on the eye of the subject with the axis coincident with the optical axis of the eye.

5. A device as claimed in claim 1 wherein the cap surface covers the outer surface of the optically scattering mass.

6. A device as claimed in claim 5 wherein the one or more optical fibers include a transmission optical fiber having a distal end disposed within the cavity.

7. A device as claimed in claim 1 wherein the optically scattering mass has a concave inner surface.

8. A device as claimed in claim 1 wherein the structure forms a shell having outer and inner surfaces conforming to the shape of the eye.

9. A device as claimed in claim 8 wherein the shell is less than 3 mm thick.

10. A device as claimed in claim 2 further comprising a transmission fiber in optical communication with the optically scattering fiber, the transmission fiber extending from the structure.

11. A device as claimed in claim 1 further comprising a photodetector in optical communication with the mass, the photodetector capable of providing a signal representing the power of the light scattered by the mass.

12. A device as claimed in claim 1 further comprising a liquid supply conduit extending from the contact lens structure, the liquid supply conduit communicating with the inner surface of the structure.

13. A device as claimed in claim 1 wherein the reflector is has specular reflectivity.

14. A device as claimed in claim 1 wherein the reflector has diffuse reflectivity.

15. A device as claimed in claim 1 wherein the ledge surface faces the inner surface of the mass and wherein the ledge surface defines an aperture.

16. A device as claimed in claim 1 wherein the reflector and the cavity entirely surround the axis.

* * * * *